United States Patent [19]

Pozzi et al.

[11] Patent Number: 5,445,828
[45] Date of Patent: Aug. 29, 1995

[54] PROGRAMMED RELEASE ORAL SOLID PHARMACEUTICAL DOSAGE FORM

[75] Inventors: Franco Pozzi, Como; Pia Furlani, Milan, both of Italy

[73] Assignee: Zambon Group S.p.A., Vicenza, Italy

[21] Appl. No.: 179,227

[22] Filed: Jan. 10, 1994

Related U.S. Application Data

[60] Division of Ser. No. 15,669, Feb. 9, 1993, Pat. No. 5,310,558, which is a continuation of Ser. No. 724,930, Jul. 2, 1991, abandoned.

[30] Foreign Application Priority Data

Jul. 4, 1990 [IT] Italy ................................ 20849/90
Dec. 19, 1990 [IT] Italy ................................ 22442/90

[51] Int. Cl.⁶ ........................ A61K 9/42; A61K 9/56
[52] U.S. Cl. ........................... 424/476; 424/458; 424/459; 424/462; 424/463; 424/474; 424/475; 424/482

[58] Field of Search .............. 424/458, 459, 463, 476, 424/474, 498

[56] References Cited

U.S. PATENT DOCUMENTS 5,023,108  6/1991  Bagaria et al. ..................... 427/3
5,270,055  12/1993  Moest ................................. 424/476

*Primary Examiner*—Thurman K. Page
*Assistant Examiner*—James M. Spear
*Attorney, Agent, or Firm*—Oblon, Spivak, McClelland, Maier & Neustadt

[57] ABSTRACT

A programmed release pharmaceutical dosage form comprising a core, containing the active ingredient, coated by a hydrophobic layer is described. Such dosage forms release the active ingredient after a pre-established no-release interval which does not depend on physiological factors.

6 Claims, No Drawings

PROGRAMMED RELEASE ORAL SOLID PHARMACEUTICAL DOSAGE FORM

This is a division of application Ser. No. 08/015,669, filed on Feb. 9, 1993, U.S. Pat. No. 5,310,558 which is a continuation of application Ser. No. 07/724,930, filed Jul. 2, 1991, now abandoned.

The present invention relates to an oral solid pharmaceutical dosage form and, in particular, it relates to an orally administrable solid pharmaceutical dosage form from which the release of the drug begins after a programmed time interval from the administration.

Such dosage forms will be hereinafter indicated as programmed release dosage forms thus referring to an oral solid pharmaceutical dosage form which releases the active ingredient after a programmed time interval (no-release interval) from the administration, in contraposition to prompt release dosage forms which release the active ingredient practically completely at the moment of the administration and to controlled release dosage forms which slowly and gradually release the active ingredient starting from the moment of the administration.

A programmed release pharmaceutical dosage form is useful for the treatment of various pathologies.

It is known, in fact, that the treatment of many pathologies requires high hematic concentrations of drug in a restricted time and, preferably, also at an established time (Novel Drum Delivery and Its Therapeutic Application—Edited by L. F. Prescott & W. S. Nimmo John Wiley & Sons—Chichester 1989).

Examples of such treatments are those directed to pathologies involving biological processes subjected to circadian rhythms [Clinical Pharmacokinetics, 7, 401, (1982)] such as the regulation of the blood pressure, the hormonal release and the chronobiology of asthma. Another example is the treatment of myocardial infarction and other cardiac diseases.

Further examples are the treatments involving rapidly metabolized drugs or drugs acting on receptors which are inactivated by a long lasting interaction with the drug (tolerance).

For such treatments a prompt release dosage form has the inconvenience to require several daily administrations while a controlled release dosage form fails to achieve a therapeutic concentration. Consequently, the programmed release of drugs such as for example antihypertensives, hormones, cardiotonics, antiasthmatics, antitussives allows to optimize the beneficial effects of the drugs by reducing their side-effects.

In addition, a suitable no-release interval can represent a mean to assure the site-specific release within particular regions of the gastro-intestinal tract, for example, within the colon. This is particularly useful for the treatment of colon pathologies such as local infections, local spasms, tumors, ulcerous colitis and Chron's disease.

The colon, moreover, represents the best site for the release of certain systemically acting drugs.

In fact, it is known that the release of certain systemically acting drugs within the colon represents a valuable solution for the systemic absorption of drums which are not orally administrable because susceptible to the action of the digestive enzymes (Science, 233, 1081-84, 1986).

Specific examples of drugs which ape susceptible to the action of the digestive enzymes are peptides and proteins, such as insulin, gastrin, pentagastrin, calcitonin, glucagon, growth hormone, corticotropin, enkephalins, oxytocin, parathyroid hormone, vasopressin and the like.

Up to now only suppository pharmaceutical forms have been developed for the release of drugs within the colon. However, such pharmaceutical forms are not always able to assure an effective release within the colon [Int. J. Pharm., 25, 191-197, (1985)].

The therapeutic importance of a programmed release orally administrable dosage form, for example in the above illustrated applications, prompted many Researchers in the Pharmaceutical Industry as well as in the University to devote relevant efforts to achieve such a goal.

To the best of our knowledge, however, no programmed release orally administrable dosage form is yet available on the market. European Patent Application No.. 040590 (Aktiebolaget Hassle) describes an oral pharmaceutical form in which a core containing the active ingredient is coated by an anionic polymer, soluble at a pH higher than 5.5, and by a water-insoluble layer.

However, this pharmaceutical form cannot assure the effective release within the colon since the release of the active ingredient, being pH dependent, can begin after only 1-2 hours from the administration.

International Patent Application No. WO 83/00435 (J. B . Tillot Ltd.) describes a solid oral form coated only by an anionic polymer which does not dissolve while passing through the upper gastro-intestinal tract. In order to assure the integrity of this solid oral form up to the colon, however, large amounts of the anionic polymer are necessary.

Moreover, also the release of this dosage form is pH dependent. In European Patent Application No. 366621 in the name of Istituto De Angeli S.p.A., a multilayered tablet for the release of a drug after a suitable time interval and especially in the colon is described. Such a pharmaceutical dosage form consists of a cope and of an outer coating.

The coating consists of an inner layer of an anionic copolymer, containing a suitable plasticizer, of an intermediate layer of a gelling polymer and, finally, of an outer layer of a gastro-resistant polymer.

Such a tablet too has the inconvenient to be pH dependent.

Since the pH value of the gastro-intestinal tract is variable, also within physiological ranges (see for example Novel Drug Delivery and Its Therapeutic Application, above cited, Chapter 9, page 91-92) pH dependent pharmaceutical dosage forms do not always warrant an effective release of the drug at the programmed times and sites. Beside the above described pH dependent dosage forms, another approach studied for obtaining the release of a drug in the intestine is that of using a coating of a material susceptible to enzymatic degradation (see for example European Patent Application No. 343993—Agric. and Food Res.; International Patent Application No. WO 87/01588—Soc. Etud. Ile-de-France; U.S. Pat. No. 4,663,308—Medical College of Ohio).

With this approach too, the release of the drug depends on physiological factor which can vary from individuals to individuals. British Patent No. 1,346,609 in the name of Daiichi Seiyaku Company Limited and European Patent Application No. 27473 in the name of Pharmaidea S.r.l. describe multilayered tablets containing the active ingredient mixed with a superdisintegrant.

Each tablet is completely coated, except for a face, with an impermeable substance while the free face is coated with a layer of gelling and/or permeable material.

The water, which penetrates through the permeable layer, swells the superdisintegrant so splitting off the permeable layer and allowing the release of the drug.

It is clear to the man skilled in the art the very difficult industrial realization of such pharmaceutical dosage forms which require particular care in selectively coating all the surfaces of the tablet, except one, with an impermeable substance and then in coating the free face with a permeable material.

To the best of our knowledge, no industrial machinery is yet available for achieving such a selective surface coating.

A pharmaceutical dosage form constituted by spheres containing an inert core, for example a sugar core, coated with a drug and further coated with a disintegrant and, finally, with an outer coating of a water-insoluble and permeable material has been described in U.S. Pat. No. 4,871,549 in the name of Fujisawa Pharm. K.K.

The spheres, which have a diameter of about 1 mm, release the drug after a certain period which depends on the thickness of the outer coating, by means of the explosion of such coating due to the swelling of the disintegrant, which constitutes the intermediate layer. However, some drugs cannot be film coated onto the core making this pharmaceutical dosage form not always suitable.

Moreover, it is particularly difficult from a technological point of view to obtain a homogeneous thickness of the water-insoluble outer layer of the spheres because of their very small diameter.

In fact, the only practical realization of this dosage form under development, as far as we know, consists of a mixture of small spheres having different thickness of the water-insoluble outer layer so obtaining a controlled release.

An object of the present invention is that of providing an orally administrable solid pharmaceutical dosage form which releases the drug after a programmed time interval from the administration.

Another object of the present invention is that of providing an orally administrable solid pharmaceutical dosage form which releases the drug after a programmed time interval and which can be easily prepared in industrial scale by means of normally available industrial machinery and standard procedures.

Another object of the present invention is that of providing an orally administrable solid pharmaceutical dosage form which releases the drug after a programmed time interval that does not depend on the pH of the gastro-intestinal tract.

Still another object of the present invention is that of providing an orally administrable solid pharmaceutical dosage form which releases the drug after a programmed time interval that shows minimum variations among different individuals.

A further object of the present invention is that of providing an orally administrable solid pharmaceutical dosage form suitable for delivering a drug in the colon.

These and other objects which will be evident to the man skilled in the art are achieved by a pharmaceutical dosage form prepared by coating a normal orally administrable solid pharmaceutical preparation with a layer comprising a mixture of a hydrophobic material with a surfactant and optionally a water-soluble film forming material.

Therefore, object of the present invention is a programmed release oral solid pharmaceutical dosage form comprising an orally administrable core, containing the active ingredient, coated by a layer comprising a mixture of a hydrophobic material having a melting point between 50° C. and 90° C. and a surfactant having a HLB value between 10 and 16, the amount of the surfactant being from 5 to 20% by weight with respect to the hydrophobic material, and optionally a water-soluble film forming material in an amount of from 5 to 30% by weight with respect to the hydrophobic material.

For the sake of simplicity, we indicate hereinafter the layer comprising a mixture of a hydrophobic material with a surfactant and optionally a water-soluble film forming material, according to the invention, as "the hydrophobic layer".

From the programmed release dosage form object of the invention the drug is released after a pre-established time interval which depends mainly on the thickness of the hydrophobic layer while it is independent of the pH value as well as of the motility of the gastro-intestinal tract.

At the end of this time interval, the drug is released with a kinetics which depends only on the kind of the pharmaceutical preparation constituting the cope of the dosage form.

In other words, after the programmed time interval the drug is released rapidly if the cope is a prompt release preparation or is released slowly if the core is a controlled release preparation. This second alternative is particularly useful as fat as drubs for the specific treatment of the colon are concerned.

Thus, the core of the dosage form object of the present invention is any solid orally administrable pharmaceutical preparation and, in particular, prompt release or controlled release tablets and capsules.

The hydrophobic material in the hydrophobic layer is constituted by fats or other hydrophobic substances having a melting point between 50° C. and 90° C.

Examples of useful hydrophobic materials are esters of higher fatty acids with higher alcohols, higher alcohols, higher fatty acids, esters of glycerin with higher fatty acids, esters of higher fatty acids with polyethyleneglycol and mixtures of two or more thereof.

Specific examples are carnauba wax, beeswax, cetyl alcohol, stearyl alcohol, hard paraffin, microcrystalline wax of petroleum wax, stearic acid, myristic acid, hydrogenated castor oil, tallow and mixtures of two or more thereof.

Preferably, the surfactant in the hydrophobic layer is selected among non-ionic surfactants or mixtures thereof.

Suitable surfactants are esters of polyethoxylated fatty acids with sorbitan and ethoxylated fatty alcohols.

The amount of surfactant is between 5 and 20% by weight with respect to the hydrophobic material and preferably about 10%.

Further examples of substances useful as the hydrophobic layer, according to the invention, are the substances known as "Gelucire" (trademark of Gattefossé Company), that is mixtures of mono-, di- and tri-glycerides and di-esters of polyethylene glycol.

The water soluble film forming material in the hydrophobic layer is an optional because its main function is that of ensuring the adhesion of the hydrophobic layer on the core.

When used, it is used in the minimum amount useful for ensuring the adhesion and this amount is between 5 and 30% by weight with respect to the hydrophobic material, preferably about 15-20%.

Exclusively for practical reasons, it is preferred to use the water-soluble film forming material.

Examples of water-soluble film forming materials are hydroxyalkylcelluloses, polymethacrylic acid esters and polyvinylpyrrolidone.

It is worth noting that all the components of the hydrophobic layer of the invention are well-known and pharmaceutically acceptable materials, most of which being already approved by the Pharmacopoeias of several Countries. This represents a relevant advantage of our dosage form.

In this connection, we wish to underline that, even if these materials are well-known in pharmaceutical technology, they have only been used in different ratios and for different aims with respect to the present invention.

For example, it is known the use of hydrophobic materials, such as waxes, also in admixture with a surfactant or with a film-forming material for the preparation of controlled release dosage forms (Sustained and Controlled Release Drum Delivery System—Edited by Joseph R. Robinson—Marcel Dekker, Inc.—New York and Basel; J. C. Colbert—Controlled Action Drug Forms—Noyes Data Corporation 1974), for the preparation of enteric coating (European Patent Application No. 195476—The Procter and Gamble Co.) or for taste-masking purposes (U.S. Pat. No. 4,341,562 —Sankyo Co. Ltd.).

The pharmaceutical dosage forms object of the invention are suitable for the administration of many drugs in the treatment of various pathologies.

In practice, all the drugs which have physico-chemical characteristics suitable for the preparation of a solid pharmaceutical preparation, like tablets and capsules, can be used.

Examples of drums which, in the treatment of the above reported pathologies, receive a therapeutical advantage from the instant dosage forms are: antihypertensive, antiasthmatic, mucolytic, antitussive, antiallergic, anti-inflammatory, antirheumatic, antiarthritic, cardiotonic, antispasmodic, hypnotic, anxiolytic, antineoplastic, analgesic and antibacterial drugs, proteins and hormones and also drugs useful in veterinary field.

Specific examples are: hydralazine, minoxidil, prazosin, enalapril, broxaterol (USAN and the USP Dictionary of Drug Names, 1991, United States Pharmacopoeial Convention Inc.), albuterol, dextromethorphan, cromolyn, acetylcysteine, dropropizine, ibuprofen, diclofenac, naproxen, aspirin, ketorolac, mesalamine, indomethacin, sulfasalazine, diltiazem, ibopamine, isosorbide mono- and di-nitrate, nitroglycerin, propranolol, oxprenolol, alprenolol, cimetropium bromide, insulin, gastrins, pentagastrin, calcitonin, glucagon, somatotropin, ACTH, endorphins, oxytocin, papathyroid hormone, vasopressin, cortisone, corticosterone, alprazolam, triazolam, oxazepam and zolpidem, optionally as salts with pharmaceutically acceptable acids or bases and, when the drugs are chiral, also in an optically active form. If not otherwise specified, for a comprehensive reference to the above listed drugs see The Merck Index, eleventh edition, 1989, published by Merck & Co., Inc.

The preparation of the dosage form of the invention is carried out according to usual procedures and by means of standard machineries. In practice, a dispersion or solution in water or in organic solvent of the hydrophobic material, the surfactant and, optionally, the water-soluble film forming material is film coated on a core containing the active ingredient.

The coating is carried out according to conventional film coating methods.

The core is a prompt release or controlled release pharmaceutical composition consisting of the active ingredient in admixture with suitable excipients.

If necessary, the core can be protected by a water-soluble film before coating with the hydrophobic layer.

By means of the pharmaceutical dosage form object of the invention, the no-release interval may be programmed by selecting the appropriate thickness of the hydrophobic layer and, the thickness being equal, by selecting the kind of hydrophobic material.

Obviously, the thickness of the hydrophobic layer is determined by its weight.

Inside the indicated melting point range, lower melting hydrophobic materials result in a longer no-release interval.

On the contrary, inside the indicated weight range, the amount of surfactant in the hydrophobic layer does not significantly influence the no-release interval.

In the same way, the site of the release may be programmed too. For the practical realization, the dosage form consisting of the core and the hydrophobic layer is preferably used when the goal is the release of the active ingredient after a pre-established time interval from the administration, independently of the site in which the release occurs.

In this case, depending on the posology of the drug to be administered, it may be useful to associate a prompt release dosage form to the programmed release dosage form of the invention, so obtaining two doses of active ingredient at different times with one administration.

This realization may be useful also in order to obtain the contemporaneous administration of two different active ingredients, so acting at different times, with one administration.

These results may be achieved by contemporaneously administering a prompt release dosage form and a programmed release dosage form of the invention, for example, in a capsule containing both of them. In alternative, the same result may be achieved by further coating a programmed release dosage form of the invention with an outer prompt release layer containing the same or another active ingredient. When the goal is the release of a drug in a specific target site, e.g. the colon, the selection of the appropriate hydrophobic layer will take into account the time necessary for the transit through the stomach as well as the time necessary for the transit through the small intestine.

However, the time necessary for the transit through the stomach can vary within a large range, from some minutes to several hours, depending mainly on the presence or not of food.

This fact is not relevant when the goal is the release of a drug after a pre-established time interval, while it becomes important when the goal is the release of a drug in the colon.

Therefore, in this second case, the dosage form should be administered between meals or after a light meal.

In alternative, by coating the dosage form of the invention with an enteric coating, that is a gastro-resistant coating, the selection of the appropriate hydrophobic layer will take into account the time necessary for the transit through the small intestine only, the no-release interval of this enteric coated dosage form being independent of the time necessary for the transit through the stomach. The enteric film coating is carried out with conventional methods by using known enteric polymers in an organic solvent or in aqueous solvent.

Suitable polymers for the enteric coating are, for example, cellulose acetate phthalate, methacrylic acid-methacrylic acid ester copolymers, hydroxypropylmethylcellulose phthalate, polyvinyl acetate phthalate, hydroxyethylcellulose phthalate, cellulose acetate tetraphthalate.

To the above indicated polymers, suitable plasticizers such as, for example, polyethylene glycol, dibutylphthalate, diethylphthalate, triacetin, castor oil, titrates may be optionally added.

Furthermore, talc or other lubricants and optionally coloring agents for pharmaceutical use may be added to the enteric film in order to improve the final characteristics of the product.

Thus practical embodiments of the pharmaceutical dosage form according to the invention are:

- a tablet constituted by a prompt release core, containing the active ingredient, coated by the hydrophobic layer
- a tablet constituted by a controlled release core, containing the active ingredient, coated by the hydrophobic layer
- a tablet constituted by a prompt release core, containing the active ingredient, coated by the hydrophobic layer and further coated by an outer prompt release layer containing the same or another active ingredient
- a capsule, containing the active ingredient, coated by the hydrophobic layer
- a capsule, containing the active ingredient, coated by the hydrophobic layer and by an outer enteric coating
- a capsule containing a prompt release tablet and a programmed release tablet
- a tablet constituted by a prompt release core, containing the active ingredient, coated by the hydrophobic layer and by an outer enteric coating
- a tablet constituted by a controlled release core, containing the active ingredient, coated by the hydrophobic layer and by an outer enteric coating.

It is not yet clear the mechanism by which the dosage form of the invention affords the release of the drum after a pre-established time interval from the administration.

Since this result does not depend on the pH and on the specific gastro-intestinal tract (as shown in example 2), it appears that it does not depend on chemical or biochemical reactions.

Tentatively, the observed effect may be explained by a physical interaction of the dosage form with the body fluids resulting in a slow and uniform dispersion of the hydrophobic layer until the intact core gets in contact with the body fluids and the drug is released.

In view of the fact that the mechanism by which the release delayed is not yet known, it may be difficult to precisely forecast the duration of such interval a priori.

However, the desired no-release interval results to be a direct function of the thickness (i.e. weight) of the hydrophobic layer, as shown in Example 19, and to a lesser extent it is a function of the other parameters, in particular the melting point of the hydrophobic material.

A very good correlation exists between a simple and readily available in vitro release test and the observed in vivo release. The in vitro test, which is herewith provided in details in example 1, shows how the in vitro no-release interval corresponds to the average no-release interval in human beings (see examples 2 and 3) with a very good correlation.

Accordingly, the examples reported in the specification give to the man of the art a sufficient guidance for the selection of the parameters affording the desired no-release interval and the simple in vitro test confirm the expected result or gives guidance for modifying the selected parameters inside the range provided by the invention.

The pharmaceutical dosage form object of the invention shows several advantages with respect to the prior art.

First of all, the programmed release of the drug makes the pharmaceutical dosage form object of the invention suitable for various drugs which are used in pathologies subjected to biological rhythms thus optimizing the beneficial effects and decreasing their side-effects.

The programmed release of the drug within particular regions of the gastro-intestinal tract, especially within the colon, makes the pharmaceutical dosage form object of the invention suitable for several drugs for which a different release-site causes a detrimental or less useful therapeutical effect.

It is possible to prepare such pharmaceutical dosage forms in a simple and economic way by using conventional methods and machineries.

The no-release interval does not depend on the pH of the gastro-intestinal tract or on other physiological parameters. This advantage, which is relevant with respect to known compositions having the same purpose, makes the dosage form of the invention suitable also, for example, for patents having a not physiologic gastro-intestinal pH, such as patients suffering from achlorhydria or taking $H_2$-antagonists or antiacids.

With the aim to better illustrate the present invention the following examples are now given.

The present invention is not intended to be limited in scope by the following examples since each is intended merely as an illustration of the invention.

Modifications of the invention in addition to those shown and described herein become apparent to the man skilled in the art from the foregoing description and from the examples.

Such modifications are intended to fall within the scope of the invention.

EXAMPLE 1

General Procedure

Preparative methods

The preparation of the copes, on which the hydrophobic layer is affixed, was carried out by using usual excipients and conventional preparative techniques.

By film coating according to known methods (coating pan of fluidized bed), the thus obtained copes were coated with a previously prepared dispersion containing the hydrophobic material, the surfactant and, optionally, the water-soluble film forming material.

The preparation of this dispersion was carried out by melting the hydrophobic material with the surfactant at a temperature between 80° and 90° C., then, by adding subsequent small portions of boiling water under suitable stirring and, finally, by cooling up to temperature.

When used, an aqueous solution of the water-soluble film forming material, prepared by adding the water-soluble film forming material to boiling water under stirring and by cooling up to room temperature, was added to the dispersion. The resultant suspension was filtered (180 mesh), then film coated on the cores and dried under air flow.

Before film coating, the copes may be protected by a water-soluble film.

The final pharmaceutical dosage forms can be further coated with an outer layer of enteric coating.

The preparation of the enteric coating can be, for example, carried out by diluting a commercially available aqueous dispersion and by affixing it on the dosage form of the invention by usual film coating techniques (coating pan or fluidized bed).

If not otherwise specified, the excipients used for the preparation of the pharmaceutical dosage forms described in the following examples are:

Polyvinylpyrrolidone: the material commercialized by BASF Company with the trademark "Kollidon K 30" was used.

Crospovidone: crosslinked polyvinylpyrrolidone commercialized by BASF Company with the trademark "Kollidon CL" was used.

Colloidal Silica: the material commercialized by Degussa Company with the trademark "Aerosil 200" was used.

Surfactant: polysorbate 80 commercialized by ICI Americas Company with the trademark "Tween 80" was used. (HLB 15 ±1)

Enteric polymer: mathacrylic acid-methacrylic acid ester copolymer commercialized by Röhm Pharm. Company with the trademark "Eudragit L30D" was used.

PEG 6000: polyethylene glycol 6000 (Merck Index, XI Ed., No. 7545, page 1204)

Hydroxypropylmethylcellulose: hydroxypropylmethylcellulose having viscosity=5 cP was used for the water-soluble film. hydroxypropylmethylcellulose having viscosity=15 cP was used for the hydrophobic layer.

In vitro release evaluation

The in vitro release of the active ingredient was determined by dissolution test (Apparatus 2 and 3, USP XXII, page 1578-1583). The in vitro evaluation was carried out in Apparatus 2 at 100 r.p.m. The obtained data were confirmed by carrying out the same test at 50 r.p.m., in water, in simulated enteric medium, in pH 1.2 buffer, in pH 5.5 buffer, in pH 6.8 buffer and in Apparatus 3 without disks. The obtained data confirmed that the no-release interval is independent of the pH.

In vivo release evaluation

The in vivo release of the active ingredient was determined by gamma scintigraphy [S. S. Davis, "Evaluation of the gastro-intestinal transit of pharmaceutical dosage form using the techniques of gamma scintigraphy", S.T.P. Pharma, 2, 1015-1022, (1986)].

For the evaluation of the time of the release as well as of the site of the release, samarium oxide was used as a component of the cope. The pharmaceutical dosage forms were irradiated and the resultant labelled dosage forms were administered to healthy volunteers. The gamma radiation was recorded by gamma camera.

Correlation between in vivo and in vitro data

The comparison between the in vivo and the in vitro release data shows a linear correlation.

In particular the in vitro no-release interval determined by the in vitro test carried out in a 3.3% sodium chloride aqueous solution gives substantially the same values as the observed in vivo no-release interval, while the in vitro no-release interval determined by a test carried out in water is half that observed in vivo.

EXAMPLE 2

Preparation of labelled tablets for the in vivo and in vitro release evaluation

The copes were prepared by conventional compression methods, each having the following composition:

| | |
|---|---|
| E110 dye | 3.0 mg |
| samarium oxide (enriched in $^{152}$Sm) | 2.0 mg |
| lactose | 77.5 mg |
| corn starch | 13.5 mg |
| polyvinylpyrrolidone | 3.0 mg |
| magnesium stearate | 1.0 mg |

The thus obtained cores were coated with a protecting water-soluble film constituted by:

| | |
|---|---|
| hydroxypropylmethylcellulose | 0.75 mg |
| PEG 6000 | 0.08 mg |

Then, the protected cores were coated with a hydrophobic layer (prepared and applied as described in example 1) constituted by:

| | |
|---|---|
| carnauba wax | 32.3 mg |
| beeswax | 13.8 mg |
| surfactant | 4.6 mg |
| hydroxypropylmethylcellulose | 9.2 mg |

In vitro release evaluation

The in vitro release evaluation was carried out by dissolution test according to what described in example 1.

The test was carried out by using a 3.3% sodium chloride aqueous solution (500 ml) at 37° C.

At specific time intervals, a specimen was withdrawn and spectrophotometrically analyzed (482 nm) to detect the presence and the amount of the dye (E110) released by the core.

The following data were obtained:

| time (min) | percentage of release |
|---|---|
| 180 | 0 |
| 190 | 0 |
| 200 | 0 |
| 210 | 0 |
| 220 | 0 |
| 230 | 0 |
| 240 | 0 |
| 310 | 5.06 |
| 330 | 59.76 |
| 360 | 102.93 |

The dissolution test was carried out also in water only (500 ml). The release of the dye was observed at halved time intervals.

In vivo release evaluation

The in vivo release evaluation was carried out by gamma scintigraphy according to what described in example 1.

The tablets were administered to seven healthy volunteers after a light meal.

The following data were obtained.

| volunteer | tablet disintegration (min) |
|---|---|
| 1 | 300 |
| 2 | 299 |
| 3 | 376 |
| 4 | 331 |
| 5 | 393 |
| 6 | 315 |
| 7 | 314 |
| mean value | 332.6 |
| standard error mean | 14.1 |

In each volunteer the proximal colon was the release-site. The in vivo release evaluation was carried out also by administering the same tablets to six different healthy volunteers after a heavy meal.

The following data were obtained.

| volunteer | tablet disintegration (min) |
|---|---|
| 1 | 287 |
| 2 | 417 |
| 3 | 304 |
| 4 | 380 |
| 5 | 304 |
| 6 | 379 |
| mean value | 345.2 |
| standard error mean | 21.8 |

The obtained data show that there is a good correlation between in vivo and in vitro release and that, with particular reference to the mean values, the food has substantially no influence upon the release-time.

Moreover, the standard error mean shows how the no-release interval has a minimum variation among different individuals.

These in vivo data further confirm the in vitro data concerning the independence of the no-release interval with respect to the pH of the gastro-intestinal tract.

EXAMPLE 3

Preparation of labelled tablets for the in vivo and in vitro release evaluation

The cores were prepared in a similar way to that described in example 2.

The thus obtained cores were coated with a protecting water-soluble film constituted by:

| hydroxypropylmethylcellulose | 0.57 mg |
|---|---|
| PEG 6000 | 0.06 mg |

Then, the protected cores were coated with a hydrophobic layer (prepared and applied as described in example 1) constituted by:

| carnauba wax | 24.6 mg |
|---|---|
| beeswax | 10.6 mg |
| surfactant | 3.5 mg |
| hydroxypropylmethylcellulose | 7.1 mg |

In vitro release evaluation

The in vitro release evaluation was carried out by dissolution test according to what described in example 1.

The test was carried out by using a 3.3% sodium chloride aqueous solution (500 ml) at 37° C.

At specific time intervals, a specimen was withdrawn and spectrophotometrically analyzed (482 nm).

The following data were obtained:

| time (min) | percentage of release |
|---|---|
| 90 | 0 |
| 105 | 0 |
| 120 | 0 |
| 135 | 0 |
| 150 | 0 |
| 165 | 0 |
| 180 | 13.87 |
| 195 | 59.6 |
| 210 | 99.2 |

The dissolution test was carried out also in water only (500 ml). The release of the dye was observed at halved time intervals.

In vivo release evaluation

The in vivo release evaluation was carried out by gamma scintigraphy according to what described in example 1.

The tablets were administered to six healthy volunteers after a light meal.

The following data were obtained:

| volunteer | tablet disintegration (min) |
|---|---|
| 1 | 206 |
| 2 | 189 |
| 3 | 188 |
| 4 | 189 |
| 5 | 225 |
| 6 | 225 |
| mean value | 203.7 |
| standard error mean | 7.3 |

The obtained data show that there is a good correlation between in vivo and in vitro release.

EXAMPLE 4

Preparation of labelled enteric coating tablets for the in vivo evaluation of the release-site The cores were prepared in a similar way to that described in example 2.

The thus obtained cores were coated with a protecting water-soluble film constituted by:

| hydroxypropylmethylcellulose | 0.75 mg |
|---|---|
| PEG 6000 | 0.08 mg |

Then, the protected copes were coated with a hydrophobic layer (prepared and applied as described in example 1) constituted by:

| carnauba wax | 30.0 mg |
|---|---|
| beeswax | 13.0 mg |
| surfactant | 4.3 mg |
| hydroxypropylmethylcellulose | 8.6 mg |

A further enteric coating constituted by:

| | |
|---|---|
| enteric polymer | 8.8 mg |
| triacetin | 0.8 mg | was affixed.

In vivo evaluation of the release-site

The in vivo evaluation of the release-site was carried out by gamma scintigraphy according to what described in example 1.

The tablets were administered to six healthy volunteers after a light meal.

In each volunteer the colon was the release-site.

EXAMPLE 5

Preparation of tablets containing Ibopamine hydrochloride as active ingredient

The cores were prepared by conventional compression methods, each having the following composition:

| | |
|---|---|
| Ibopamine hydrochloride | 55.95 mg |
| polyvinylpyrrolidone | 1.48 mg |
| crospovidone | 45.83 mg |
| colloidal silica | 0.42 mg |
| stearic acid | 0.42 mg |

The thus obtained cores were coated with a protecting water-soluble film constituted by:

| | |
|---|---|
| hydroxypropylmethylcellulose | 0.20 mg |
| PEG 6000 | 0.02 mg |

Then, the protected cores were coated with a hydrophobic layer (prepared and applied as described in example 1) constituted by:

| | |
|---|---|
| carnauba wax | 56.29 mg |
| surfactant | 5.63 mg |
| hydroxypropylmethylcellulose | 11.26 mg |

In vitro release evaluation

The in vitro release evaluation was carried out by dissolution test according to what described in example 1.

The test was carried out by using water (900 ml) at 37° C. At specific time intervals, a specimen (10 ml) was withdrawn and spectrophotometrically analyzed (220 nm).

The following data were obtained:

| time (min) | percentage of release |
|---|---|
| 0 | 0 |
| 30 | 0 |
| 60 | 0 |
| 90 | 0 |
| 120 | 0 |
| 150 | 8.92 |
| 180 | 88.30 |
| 210 | 97.13 |

EXAMPLE 6

Preparation of tablets containing Ibopamine hydrochloride as active ingredient

The cores were prepared by conventional compression methods, each having the following composition:

| | |
|---|---|
| Ibopamine hydrochloride | 42.00 mg |
| polyvinylpyrrolidone | 1.65 mg |
| microcrystalline cellulose | 6.55 mg |
| colloidal silica | 0.40 mg |
| stearic acid | 1.80 mg |
| lactose | 33.70 mg |

The thus obtained cores were coated with a protecting water-soluble film constituted by:

| | |
|---|---|
| hydroxypropylmethylcellulose | 2.67 mg |
| PEG 6000 | 0.30 mg |

Then, the protected cores were coated with a hydrophobic layer (prepared and applied as described in example 1) constituted by:

| | |
|---|---|
| carnauba wax | 29.33 mg |
| surfactant | 2.93 mg |
| hydroxypropylmethylcellulose | 5.87 mg |

In vitro release evaluation

The in vitro release evaluation was carried out by dissolution test according to what described in example 1.

The test was carried out by using water (900 ml) at 37° C. At specific time intervals, a Specimen (10 ml) was withdrawn and spectrophotometrically analyzed (220 nm).

The following data were obtained:

| time (min) | percentage of release |
|---|---|
| 0 | 0 |
| 30 | 0 |
| 60 | 0 |
| 90 | 35.11 |
| 120 | 101.43 |

EXAMPLE 7

Preparation of tablets containing Broxaterol hydrochloride as active ingredient

The cores were prepared by conventional compression methods, each having the following composition:

| | |
|---|---|
| Broxaterol hydrochloride | 0.569 mg |
| polyvinylpyrrolidone | 3.000 mg |
| lactose | 39.531 mg |
| starch | 56.000 mg |
| magnesium stearate | 1.000 mg |

The thus obtained cores were coated with a protecting water-soluble film constituted by:

| | |
|---|---|
| hydroxypropylmethylcellulose | 0.90 mg |
| PEG 6000 | 0.10 mg |

Then, the protected cores were coated with a hydrophobic layer (prepared and applied as described in example 1) constituted by:

| | |
|---|---|
| carnauba wax | 15.24 mg |
| beeswax | 6.53 mg |

| | |
|---|---|
| surfactant | 2.18 mg |
| hydroxypropylmethylcellulose | 4.35 mg |

In vitro release evaluation

The in vitro release evaluation was carried out by dissolution test according to what described in example 1.

The test was carried out by using water (500 ml) at 37° C. At specific time intervals, a specimen was withdrawn and analyzed by reversed-phase HPLC chromatography (RP 8 column, 7 μm; eluent phosphate buffer-/acetonitrile; UV detector at 216 nm).

The following data were obtained:

| time (min) | percentage of release |
|---|---|
| 0 | 0 |
| 30 | 0 |
| 60 | 0 |
| 90 | 0 |
| 120 | 60 |
| 150 | 98 |

EXAMPLE 8

Preparation of tablets containing Broxaterol hydrochloride as active ingredient

The cores were prepared by conventional compression methods, each having the following composition:

| | |
|---|---|
| Broxaterol hydrochloride | 0.569 mg |
| polyvinylpyrrolidone | 3.000 mg |
| microcrystalline cellulose | 95.531 mg |
| magnesium stearate | 1.000 mg |

The thus obtained cores were coated with a protecting water-soluble film constituted by:

| | |
|---|---|
| hydroxypropylmethylcellulose | 0.49 mg |
| PEG 6000 | 0.06 mg |

Then, the protected cores were coated with a hydrophobic layer (prepared and applied as described in example 1) constituted by:

| | |
|---|---|
| carnauba wax | 18.98 mg |
| beeswax | 8.13 mg |
| surfactant | 2.70 mg |
| hydroxypropylmethylcellulose | 5.42 mg |

In vitro release evaluation

The in vitro release evaluation was carried out by dissolution test according to what described in example 1.

The test was carried out by using water (500 ml) at 37° C. At specific time intervals, a specimen was withdrawn and analyzed by reversed-phase HPLC chromatography (RP 8 column, 7 μm; eluent phosphate buffer-/acetonitrile; UV detector at 216 nm).

The following data were obtained:

| time (min) | percentage of release |
|---|---|
| 0 | 0 |
| 30 | 0 |
| 60 | 0 |
| 90 | 0 |
| 120 | 47.3 |
| 150 | 77 |
| 180 | 100 |

EXAMPLE 9

Preparation of tablets containing Broxaterol hydrochloride as active ingredient

The cores were prepared in a similar way to that described in example 10.

The thus obtained cores were coated with a protecting water-soluble film constituted by:

| | |
|---|---|
| hydroxypropylmethylcellulose | 0.90 mg |
| PEG 6000 | 0.10 mg |

Then, the protected cores were coated with a hydrophobic layer (prepared and applied as described in example 1) constituted by:

| | |
|---|---|
| carnauba wax | 38.47 mg |
| beeswax | 16.47 mg |
| surfactant | 5.47 mg |
| hydroxypropylmethylcellulose | 10.98 mg |

In vitro release evaluation

The in vitro release evaluation was carried out by dissolution test according to what described in example 1.

The test was carried out by using water (500 ml) at 37° C. At specific time intervals, a specimen was withdrawn and analyzed by reversed-phase HPLC chromatography (RP 8 column, 7 μm; eluent phosphate buffer-/acetonitrile; UV detector at 216 nm).

The following data were obtained:

| time (min) | percentage of release |
|---|---|
| 0 | 0 |
| 30 | 0 |
| 60 | 0 |
| 90 | 0 |
| 120 | 0 |
| 150 | 0 |
| 180 | 0 |
| 210 | 0 |
| 240 | 0 |
| 270 | 33 |
| 300 | 67 |
| 330 | 102 |

EXAMPLE 10

Preparation of tablets containing Broxaterol hydrochloride as active ingredient

The cores were prepared by conventional compression methods, each having the following composition:

| | |
|---|---|
| Broxaterol hydrochloride | 0.569 mg |
| polyvinylpyrrolidone | 3.000 mg |
| lactose | 77.431 mg |
| starch | 18.000 mg |
| magnesium stearate | 1 mg |

The thus obtained copes were coated with a protecting water-soluble film constituted by:

| | |
|---|---|
| hydroxypropylmethylcellulose | 7.41 mg |
| PEG 6000 | 0.82 mg |

Then, the protected cores were coated with a hydrophobic layer (prepared and applied as described in example 1) constituted by:

| | |
|---|---|
| carnauba wax | 22.16 mg |
| beeswax | 9.50 mg |
| surfactant | 3.17 mg |
| hydroxypropylmethylcellulose | 6.33 mg |

In vitro release evaluation

The in vitro release evaluation was carried out by dissolution test according to what described in example 1.

The test was carried out by using water (500 ml) at 37° C. At specific time intervals, a specimen was withdrawn and analyzed by reversed-phase HPLC chromatography (RP 8 column, 7 μm; eluent phosphate buffer-/acetonitrile; UV detector at 216 nm).

The following data were obtained:

| time (min) | percentage of release |
|---|---|
| 0 | 0 |
| 30 | 0 |
| 60 | 0 |
| 90 | 0 |
| 120 | 70 |
| 150 | 102 |

EXAMPLE 11

Preparation of tablets containing Broxaterol hydrochloride as active ingredient

The cores were prepared in a similar way to that described in example 10.

The thus obtained cores were coated with a hydrophobic layer (prepared and applied as described in example 1) constituted by:

| | |
|---|---|
| carnauba wax | 18.96 mg |
| beeswax | 8.13 mg |
| surfactant | 2.71 mg |
| hydroxypropylmethylcellulose | 5.42 mg |

In vitro release evaluation

The in vitro release evaluation was carried out by dissolution test according to what described in example 1.

The test was carried out by using water (500 ml) at 37° C. At specific time intervals, a specimen was withdrawn and analyzed by reversed-phase HPLC chromatography (RP 8 column, 7 μm; eluent phosphate buffer-/acetonitrile; UV detector at 216 nm).

The following data were obtained:

| time (min) | percentage of release |
|---|---|
| 0 | 0 |
| 30 | 0 |
| 60 | 0 |
| 90 | 7 |
| 120 | 78 |
| 150 | 100 |

EXAMPLE 12

Preparation of tablets containing Diclofenac sodium as active ingredient

The cores were prepared by conventional compression methods, each having the following composition:

| | |
|---|---|
| Diclofenac sodium | 50.0 mg |
| microcrystalline cellulose | 10.0 mg |
| polyvinylpyrrolidone | 3.0 mg |
| lactose | 25.0 mg |
| corn starch | 74.5 mg |
| magnesium stearate | 1.5 mg |
| colloidal silica | 6.0 mg |
| sodium carboxymethylstarch | 20.0 mg |

The thus obtained cores were coated with a protecting water-soluble film constituted by:

| | |
|---|---|
| hydroxypropylmethylcellulose | 3.6 mg |
| PEG 6000 | 0.4 mg |

Then, the protected cores were coated with a hydrophobic layer (prepared and applied as described in example 1) constituted by:

| | |
|---|---|
| carnauba wax | 62.0 mg |
| beeswax | 26.5 mg |
| surfactant | 8.8 mg |
| hydroxypropylmethylcellulose | 17.7 mg |

In vitro release evaluation

The in vitro release evaluation was carried out by dissolution test according to what described in example 1.

The test was carried out by using water (600 ml) at 37° C. At specific time intervals, a specimen was withdrawn and spectrophotometrically analyzed (276 nm).

The following data were obtained:

| time (min) | percentage of release |
|---|---|
| 270 | 0 |
| 300 | 12 |
| 330 | 87.5 |
| 360 | 99.2 |

EXAMPLE 13

Preparation of tablets containing Naproxen as active ingredient

The cores were prepared by conventional compression methods, each having the following composition:

| | |
|---|---|
| Naproxen | 250 mg |
| polyvinylpyrrolidone | 15 mg |
| corn starch | 44 mg |
| magnesium stearate | 5 mg |

The thus obtained cores were coated with a protecting water-soluble film constituted by:

| | |
|---|---|
| hydroxypropylmethylcellulose | 6.0 mg |
| PEG 6000 | 0.7 mg |

Then, the protected cores were coated with a hydrophobic layer (prepared and applied as described in example 1) constituted by:

| | |
|---|---|
| carnauba wax | 104.8 mg |
| beeswax | 44.8 mg |
| surfactant | 14.9 mg |
| hydroxypropylmethylcellulose | 29.9 mg |

In vitro release evaluation

The in vitro release evaluation was carried out by dissolution test according to what described in example 1.

The test was carried out by using phosphate buffer (900 ml) at 37° C. At specific time intervals, a specimen was withdrawn and spectrophotometrically analyzed (330 nm).

The following data were obtained:

| time (min) | percentage of release |
|---|---|
| 360 | 0 |
| 390 | 16.9 |
| 420 | 73.7 |
| 450 | 104.3 |

EXAMPLE 14

Preparation of tablets containing Albuterol sulfate as active ingredient

The cores were prepared by conventional compression methods, each having the following composition:

| | |
|---|---|
| Albuterol sulfate | 2.4 mg |
| lactose | 77.5 mg |
| polyvinylpyrrolidone | 3.0 mg |
| corn starch | 16.1 mg |
| magnesium stearate | 1.0 mg |

The thus obtained cores were coated with a hydrophobic layer (prepared and applied as described in example 1) constituted by:

| | |
|---|---|
| carnauba wax | 32.3 mg |
| beeswax | 13.8 mg |
| surfactant | 4.6 mg |
| hydroxypropylmethylcellulose | 9.2 mg |

In vitro release evaluation

The in vitro release evaluation was carried out by dissolution test according to what described in example 1.

The test was carried out by using water (500 ml) at 37° C. At specific time intervals, a specimen was withdrawn and analyzed by reversed-phase HPLC chromatography (RP 8 column, 7 μm; eluent phosphate buffer/acetonitrile; UV detector at 276 nm).

The following data were obtained:

| time (min) | percentage of release |
|---|---|
| 180 | 0 |
| 190 | 18.6 |
| 200 | 50.8 |
| 210 | 71.4 |
| 220 | 92 |
| 230 | 101.2 |

EXAMPLE 15

Preparation of tablets containing Triazolam as active ingredient

The cores were prepared by conventional compression methods, each having the following composition:

| | |
|---|---|
| Triazolam | 0.125 mg |
| lactose | 72.000 mg |
| microcrystalline cellulose | 18.000 mg |
| colloidal silica | 0.300 mg |
| dioctyl sodium sulfosuccinate | 0.850 mg |
| sodium benzoate | 0.150 mg |
| corn starch | 4.750 mg |
| magnesium stearate | 1.000 mg |

The thus obtained cores were coated with a protecting water-soluble film constituted by:

| | |
|---|---|
| hydroxypropylmethylcellulose | 0.90 mg |
| PEG 6000 | 0.09 mg |

Then, the protected cores were coated with a hydrophobic layer (prepared and applied as described in example 1) constituted by:

| | |
|---|---|
| carnauba wax | 25.0 mg |
| beeswax | 10.7 mg |
| surfactant | 3.6 mg |
| hydroxypropylmethylcellulose | 7.2 mg |

In vitro release evaluation

The in vitro release evaluation was carried out by dissolution test according to what described in example 1.

The test was carried out by using water (500 ml) at 37° C. At specific time intervals, a specimen was withdrawn and analyzed by reversed-phase HPLC chromatography (RP 8 column, 7 μm; eluent water/acetonitrile; UV detector at 222 nm).

The following data were obtained:

| time (min) | percentage of release |
|---|---|
| 90 | 0 |
| 105 | 0 |
| 120 | 52.8 |
| 135 | 98.7 |
| 150 | 99.8 |

EXAMPLE 16

Preparation of tablets with controlled-release core containing

Mesalamine as active ingredient

The cores were prepared by conventional compression methods, each having the following composition:

| | |
|---|---|
| Mesalamine | 300.0 mg |
| ethylcellulose | 76.4 mg |
| crospovidone | 18.3 mg |
| magnesium stearate | 6.2 mg |
| talc | 10.4 mg |

The thus obtained cores were coated with a protecting water-soluble film constituted by:

| | |
|---|---|
| hydroxypropylmethylcellulose | 23.4 mg |
| PEG 6000 | 2.4 mg |

Then, the protected cores were coated with a hydrophobic layer (prepared and applied as described in example 1) constituted by:

| | |
|---|---|
| carnauba wax | 140 mg |
| beeswax | 60 mg |
| surfactant | 20 mg |
| hydroxypropylmethylcellulose | 40 mg |

A further enteric coating constituted by:

| | |
|---|---|
| enteric polymer | 47.0 mg |
| triacetin | 1.3 mg |
| was affixed. | |

EXAMPLE 17

Preparation of tablets with controlled-release core containing Cimetropium bromide an active ingredient The cores were prepared by conventional compression methods, each having the following composition:

| | |
|---|---|
| Cimetropium bromide | 50 mg |
| lactose | 125 mg |
| starch | 73 mg |
| magnesium stearate | 2 mg |

The thus obtained cores were coated with a protecting water-soluble film constituted by:

| | |
|---|---|
| hydroxypropylmethylcellulose | 1.20 mg |
| PEG 6000 | 0.12 mg |

Then, the protected cores were coated with a hydrophobic layer (prepared and applied as described in example 1) constituted by:

| | |
|---|---|
| carnauba wax | 67.0 mg |
| beeswax | 29.0 mg |
| surfactant | 9.6 mg |
| hydroxypropylmethylcellulose | 19.0 mg |
| A further enteric coating constituted by: | |
| enteric polymer | 17.0 mg |
| triacetin | 0.5 mg |
| was affixed. | |

EXAMPLE 18

Preparation of soft gelatin capsules for the in vitro release evaluation

Each capsule contained:

| | |
|---|---|
| E110 dye | 6 mg |
| polyethyleneglycol 600 | 194 mg |

The capsules were film coated by fluidization dip coating at a temperature below 50° C. using an aqueous dispersion of the following mixture:

| | |
|---|---|
| beeswax | 23.37 mg |
| cetostearyl alcohol | 5.85 mg |
| surfactant | 2.93 mg |
| hydroxypropylmethylcellulose | 5.85 mg |

In vitro release evaluation

The in vitro release evaluation was carried out by dissolution test according to what described in example 1.

The test was carried out using water (500 ml) at 37° C. At specific time intervals, a specimen was withdrawn and spectrophotometrically analyzed (482 nm).

The following data were obtained:

| time (min) | percentage of release |
|---|---|
| 0 | 0 |
| 30 | 0 |
| 60 | 0 |
| 90 | 0 |
| 120 | 0 |
| 150 | 78 |
| 180 | 102 |

EXAMPLE 19

Evaluation of the correlation between the thickness of the hydrophobic layer and the no-release interval The in vitro release of the protected cores, that is without the hydrophobic layer, prepared as described in example 2, and with different increasing thickness of the hydrophobic layer, prepared and applied as described in example 1, was evaluated by dissolution test according to what described in example 1.

The hydrophobic layer was constituted by a mixture of carnauba wax, beeswax, surfactant and hydroxypropylmethylcellulose in the same weight ratios described in example 2.

The increase of the thickness of the hydrophobic layer was expressed as increase of the tablet diameter and as the corresponding increase of the tablet weight.

The dissolution test was carried out by using water (500 ml) at 370C.

The beginning of the release was detected spectrophotometrically (482 nm).

The following data were obtained:

| diameter (mm) | weight increase (%) | no-release interval (min) |
|---|---|---|
| 5.50 | 0 | 0 |
| 6.10 | 28 | 75 |
| 6.50 | 48 | 135 |
| 6.75 | 60 | 155 |
| 7.00 | 73 | 180 |

The same dissolution test was carried out by using the protected cores, that is without the hydrophobic layer, prepared as described in example 5, and with different increasing thickness of the hydrophobic layer, prepared and applied as described in example 1.

The hydrophobic layer was constituted by a mixture of carnauba wax, surfactant and hydroxypropylmethylcellulose in the same weight ratios described in example 5.

The beginning of the release was detected spectrophotometrically (220 nm).

The following data were obtained:

| diameter (mm) | weight increase (%) | no-release interval (min) |
| --- | --- | --- |
| 7.2 | 0 | 0 |
| 7.3 | 11 | 15 |
| 7.4 | 20 | 30 |
| 7.7 | 40 | 90 |
| 8.0 | 69 | 140 |

The obtained data show that there is a linear correlation between the increase of the thickness of the hydrophobic layer and the increase of the no-release interval and that this correlation does not depend on the cores.

What we claim is:

1. A programmed release solid pharmaceutical composition in the form of an orally administrable tablet comprising a prompt release core, containing the active ingredient, coated by a layer Comprising a mixture of a hydrophobic material selected from the group consisting of esters of higher fatty acids with higher alcohols, higher alcohols, higher fatty acids, salts of higher fatty acids, esters of glycerine with higher fatty acids, esters of higher fatty acids with polyethyleneglycol, wax, paraffin oil and mixtures thereby having a melting point between 50° C. and 90° C. and a non-ionic surfactant having a HLB value between 10 and 16, the amount of the surfactant being from 5 to 20% by weight with respect to the hydrophobic material, and optionally a pharmaceutically acceptable water-soluble film forming material in an amount of from 5 to 30% by weight with respect to the hydrophobic material and further coated by an outer prompt release layer containing the same or another active ingredient.

2. A programmed release solid pharmaceutical composition in the form of an orally administrable capsule, comprising a core containing the active ingredient, coated by a layer comprising a mixture of a hydrophobic material selected from the group consisting of esters of higher fatty acids with higher alcohols, higher alcohols, higher fatty acids, salts of higher fatty acids, esters of glycerine with higher fatty acids, esters of higher fatty acids with polyethyleneglycol, wax, paraffin oil and mixtures thereof having a melting point between 50° C. and 90° C. and a non-ionic surfactant having a HLB value between 10 and 16, the amount of the surfactant being from 5 to 20% by weight with respect to the hydrophobic material, and optionally a pharmaceutically acceptable water-soluble film forming material in an amount of from 5 to 30% by weight with respect to the hydrophobic material.

3. A programmed release capsule according to claim 2, further comprising an outer enteric coating.

4. A capsule containing a) a prompt release tablet and b) a programmed release tablet comprising: a gore containing an active ingredient, coated by a layer comprising a mixture of a hydrophobic material selected from the group consisting of esters of higher fatty acids with higher alcohols, higher alcohols, higher fatty acids, salts of higher fatty acids, esters of glycerine with higher fatty acids, esters of higher fatty acids with polyethyleneglycol, wax, paraffin oil and mixtures thereof having a melting point between 50° C. and 90° C. and a non-ionic surfactant having a HLB value between 10 and 16, the amount of the surfactant being from 5 to 20% by weight with respect to the hydrophobic material, and optionally a pharmaceutically acceptable water-soluble film forming material in .an amount of from 5 to 30% by weight with respect to the hydrophobic material.

5. A programmed release solid pharmaceutical composition in the form of an orally administratable tablet constituted by a prompt release core, containing the active ingredient, coated by a layer comprising: a mixture of a hydrophobic material selected from the group consisting of esters of higher fatty acids with higher alcohols, higher alcohols, higher fatty acids, salts of higher fatty acids, esters of glycerine with higher fatty acids, esters of higher fatty acids with polyethyleneglycol, wax, paraffin oil and mixtures thereof having a melting point between 50° C. and 90° C. and a non-ionic surfactant having a HLB value between 10 and 16, the amount of the surfactant being from 5 to 20% by weight with respect to the hydrophobic material, and optionally a pharmaceutically acceptable water soluble film forming material in an amount of from 5 to 30% by weight with respect to the hydrophobic material and by an outer enteric coating.

6. A programmed release solid pharmaceutical composition in the form of an orally administratable tablet constituted by a controlled release core, containing the active ingredient, coated by a layer comprising a mixture of a hydrophobic material selected from the group consisting of esters of higher fatty acids with higher alcohols, higher alcohols, higher fatty acids, salts of higher fatty acids, esters of glycerine with higher fatty acids, esters of higher fatty acids with polyethyleneglycol, wax, paraffin oil and mixtures thereof having a melting point between 50° C. and 90° C. and a non-ionic surfactant having a HLB value between 10 and 16, the amount of the surfactant being from 5 to 20% by weight with respect to the hydrophobic material, and optionally a pharmaceutically acceptable water-soluble film forming material in an amount of from 5 to 30% by weight with respect to the hydrophobic material and by an outer enteric coating.

* * * * *